(12) United States Patent
Lin et al.

(10) Patent No.: US 10,172,699 B2
(45) Date of Patent: Jan. 8, 2019

(54) IMPLANTS FOR PELVIC ORGAN PROLAPSE SUPPORT

(71) Applicants: National Taiwan University, Taipei (TW); National Taiwan University Hospital, Taipei (TW); Andrew Man Chung Wo, Taipei (TW)

(72) Inventors: Ho-Hsiung Lin, Taipei (TW); Ting-Chen Chang, Taipei (TW)

(73) Assignees: NATIONAL TAIWAN UNIVERSITY, Taipei (TW); NATIONAL TAIWAN UNIVERSITY HOSPITAL, Taipei (TW); Andrew Man Chung Wo, Taipei (TW)

( * ) Notice: Subject to any disclaimer, the term of this patent is extended or adjusted under 35 U.S.C. 154(b) by 19 days.

(21) Appl. No.: 15/304,988

(22) PCT Filed: Dec. 2, 2014

(86) PCT No.: PCT/US2014/068236
§ 371 (c)(1),
(2) Date: Oct. 18, 2016

(87) PCT Pub. No.: WO2015/160386
PCT Pub. Date: Oct. 22, 2015

(65) Prior Publication Data
US 2017/0181823 A1    Jun. 29, 2017

(30) Foreign Application Priority Data
Apr. 18, 2014  (TW) .............................. 103114214 A

(51) Int. Cl.
*A61F 2/00* (2006.01)
*A61F 6/08* (2006.01)

(52) U.S. Cl.
CPC .......... *A61F 2/0045* (2013.01); *A61F 2/0063* (2013.01); *A61F 6/08* (2013.01)

(58) Field of Classification Search
CPC .... A61F 2/0004; A61F 2/0031; A61F 2/0036; A61F 2/0045; A61F 2/0063;
(Continued)

(56) References Cited

U.S. PATENT DOCUMENTS

2003/0220538 A1\* 11/2003 Jacquetin .............. A61F 2/0045
600/37
2009/0259092 A1    10/2009 Ogdahl et al.
(Continued)

FOREIGN PATENT DOCUMENTS

WO    WO 2010028242    3/2010
WO    WO 2013020076    2/2013

*Primary Examiner* — Carrie R Dorna
(74) *Attorney, Agent, or Firm* — WPAT, PC

(57) ABSTRACT

The present invention provides an implant for pelvic organ prolapse support, comprising an implant for anterior vaginal wall prolapse support which comprises first body having a first angle and a second angle, a pair of first arms and a pair of second arms. The implant for pelvic organ prolapse support of the present invention can treat cystocele and stress urinary incontinence simultaneously, and can optionally combine with an implant for posterior vaginal wall prolapse support and an auxiliary supporter to treat cystocele, stress urinary incontinence, enterocele, uterine prolapse, rectocele prolapse, anal prolapse, and vaginal vault prolapse at one time.

6 Claims, 6 Drawing Sheets

(58) Field of Classification Search
CPC ..... A61F 2250/0037; A61F 2250/0078; A61B 2017/00805
See application file for complete search history.

(56) References Cited

U.S. PATENT DOCUMENTS

| | | |
|---|---|---|
| 2009/0306464 A1 | 12/2009 | Griguol |
| 2010/0197999 A1* | 8/2010 | Deegan .............. A61B 17/0401 600/30 |
| 2010/0261955 A1* | 10/2010 | O'Hern .............. A61B 17/0401 600/37 |
| 2012/0004501 A1 | 1/2012 | Beyer |
| 2013/0079586 A1 | 3/2013 | Knipfer |

* cited by examiner

IMPLANTS FOR PELVIC ORGAN PROLAPSE SUPPORT

CROSS-REFERENCES TO RELATED APPLICATIONS

This application claims priority to Taiwan Patent Application No. 103114214 filed on 18 Apr. 2014. All disclosure of which is incorporated herein by reference in its entirety.

BACKGROUND OF THE INVENTION

1. Field of the Invention

The present invention relates to an implant for pelvic organ prolapse support. More specifically, the present invention relates to an implant that is capable of simultaneously supporting bladder, urethra, uterus, vaginal vault, intestine, rectum, and anus in female patients with pelvic organ prolapse.

2. The Prior Arts

Throughout women's lifespan, the incidence of pelvic organ prolapse (POP) is close to 50%. Approximately one tenth of the female population would receive surgeries associated with POP before age of eighty and about 30% of which may receive more than one surgery. Regarding the goal of pelvic reconstructive surgery, besides restoring organs to their normal anatomical positions, physicians also design the most appropriate surgery by taking account of urination symptom, age, physical condition, and sexual function of each patient.

It is known that the conventional pelvic reconstructive surgeries are not effective and sustainable with possibility of recurrence up to 30%. To improve such flaws, utilizing artificial mesh is the current trend and is indeed effective with regard to the short-term success rate. On the other hand, using mid-urethral sling made of artificial mesh for the treatment of stress urinary incontinence (SUI) has become a gold standard method. Clinically, if a patient has both cystocele and SUI, two artificial meshes are required to be used separately by surgery; if the patient also suffers from prolapse of other pelvic organs, even more artificial meshes are needed. Although the surgery using artificial mesh shows high success rate and is effective in terms of fixation, the effectiveness and safety of using artificial mesh in standard pelvic reconstructive surgery are still questionable and require further investigation.

Over the past few years, Food and Drug Administration of the United States constantly receives reports regarding adverse reactions of artificial meshes. More than 1,000 adverse reaction cases of using artificial mesh for the treatment of POP and SUI were reported between 2005 and 2007. In 2008 alone, 2,874 cases of adverse reaction with 3 deaths were reported. Common adverse reactions reported include: mesh extrusion, infection, pain, difficulties during sexual activity, pain during sexual activity, vaginal scar, urinary retention, or recurrence of POP or SUI. Hence, Food and Drug Administration of the United States had sent out warnings regarding the use of artificial mesh in October 2008, which indicated the possibility of severe complications caused by using artificial mesh for the treatment of POP and SUI.

As a result, for the treatment of POP and SUI, the search for alternative therapies as well as improvement of the current artificial mesh by utilizing the advantages of the good supportive characteristics and high surgical success rate thereof to conquer or overcome the possibility of complications are needed.

SUMMARY OF THE INVENTION

In order to solve the above problems, the present invention provides an implant for POP support, comprising an implant for anterior vaginal wall prolapse support which comprises: a first body having a first angle and a second angle located at both ends of a longitudinal axis of the first body; a pair of first arms connecting with both sides of the longitudinal axis of the first body, respectively; a pair of second arms connecting with both sides of the longitudinal axis of the first body, respectively, wherein the first arm and the second arm disposed at the same side of the longitudinal axis are separated from each other.

In one embodiment of the present invention, the implant for anterior vaginal wall prolapse support is a polymer mesh. The first angle of the implant for anterior vaginal wall prolapse support is an obtuse angle and the degree of the first angle of the implant for anterior vaginal wall prolapse support is greater than the degree of the second angle of the implant; the lengths of the two edges forming the first angle of the implant for anterior vaginal wall prolapse support are equal; the lengths of the two edges forming the second angle of the implant for anterior vaginal wall prolapse support are equal. In one embodiment of the present invention, each of the first arms of the implant for anterior vaginal wall prolapse support is disposed at each margin of the extended edges of the first angle of the implant for anterior vaginal wall prolapse support. In one embodiment of the present invention, each of the second arms of the implant for anterior vaginal wall prolapse support is disposed at each edge of the second angle of the implant for anterior vaginal wall prolapse support.

The implant for POP support further comprises an implant for posterior vaginal wall prolapse support, comprising: a second body having a shape of a longitudinal axis greater than a horizontal axis; a pair of third arms connecting with both sides of the longitudinal axis of the second body, respectively; a pair of fourth arms connecting with both sides of the longitudinal axis of the second body, respectively, wherein the third arm and the fourth arm disposed at the same side of the longitudinal axis are separated from each other; and a pair of fifth arms connecting with both sides of the longitudinal axis of the second body, respectively, wherein the fourth arm is located between the third and the fifth arms disposed at the same side of the longitudinal axis and the fourth arm disposed at one side of the longitudinal axis is aligned with the fifth arm disposed at another side of the longitudinal axis.

In one embodiment of the present invention, the implant for posterior vaginal wall prolapse support is a polymer mesh. The pair of fourth arms of the implant for posterior vaginal wall prolapse support is adjacent to the pair of fifth arms of the implant for posterior vaginal wall prolapse support; selectively, each of the third arms of the implant for posterior vaginal wall prolapse support has an expansion portion and the expansion portions of the third arms are disposed at symmetric locations; a shape of the expansion portion is circular.

In another embodiment of the present invention, the implant for posterior vaginal wall prolapse support further comprises a set of sixth arms disposed at one end of the longitudinal axis of the second body close to the pair of fifth arms. Preferably, the set of sixth arms of the implant for posterior vaginal wall prolapse support has three arms; the end close to the pair of third arms on the longitudinal axis of the second body having an obtuse angle.

In another embodiment of the present invention, the implant for posterior vaginal wall prolapse support comprises an auxiliary supporter comprising a plurality of fixing components and a plurality of linking components interconnecting with the plurality of fixing components, wherein the width of each fixing component of the plurality of fixing components is equal or greater than the width of each of the sixth arms of the implant for posterior vaginal wall prolapse support. Preferably, the auxiliary supporter is a polymer mesh; the shape of the plurality of fixing components is circular.

According to the technical feature of the implant for POP support of the present invention, it is able to treat cystocele and SUI simultaneously by the first angle and the pair of first arms without the use of conventional mid-urethral sling. In other words, current treatment for cystocele and SUI that requires two separate surgeries can be accomplished by only one surgery according to the present invention. Furthermore, if the patient only suffers from cystocele, the implant for anterior vaginal wall prolapse support of the present invention can be utilized to support bladder neck and proximal urethra resulting in anti-incontinence effect. Besides, the body of the implant of the present invention can support the bladder from rotary torque during bladder contraction in voiding, prevent severe urge urine leakage, reduce the occurrence of cystocele, and withstand high level of bladder urine leakage.

In another aspect, after jointly using the implant for posterior vaginal wall prolapse support and the auxiliary supporter, cystocele, SUI, enterocele, uterine prolapse, and anal prolapse can be treated in one treatment. The anterior vaginal wall relates to bladder and urethra, while the posterior vaginal wall relates to small intestine, anus, uterus, rectum, and vaginal vault. Thus, the present invention provides ligamentous supports of DeLancey's level I (Suspension), level II (Lateral attachment), and level III (Fusion), as well as reposition and fixation for the prolapsed bladder, urethra, uterus, small intestine, rectum, and anus.

The present invention is further explained in the following embodiment illustrations and examples. Those examples below should not, however, be considered to limit the scope of the invention, and it is contemplated that modifications will readily occur to those skilled in the art, which modifications will be within the spirit of the invention and scope of the appended claims.

DETAILED DESCRIPTION OF THE PREFERRED EMBODIMENT

Figure 1:
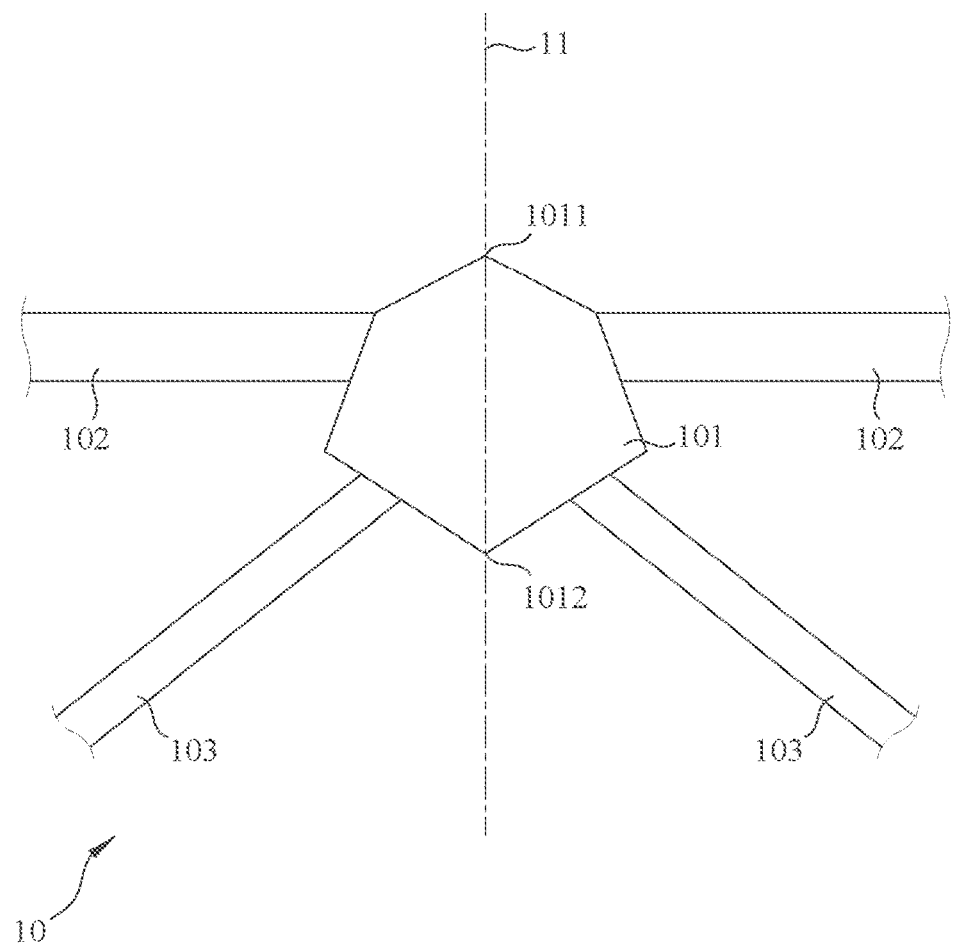
FIG. 1, schematic representation of the implant for anterior vaginal wall prolapse support of the present invention.

Please refer to FIG. 1, the schematic representation of the implant for anterior vaginal wall prolapse support 10. According to FIG. 1, the implant for anterior vaginal wall prolapse support 10 comprises a first body 101 having a first angle 1011 and a second angle 1012 located at both ends of the longitudinal axis 11 of the first body 101; a pair of first arms 102 connecting with both sides of the longitudinal axis 11 of the first body 101; a pair of second arms 103 connecting with both sides of the longitudinal axis 11 of the first body 101, wherein the first arm 102 and the second arm 103 disposed at the same side of the longitudinal axis are separated from each other. The longitudinal axis 11 runs the length of the body 101 of the implant from the first angle 1011 through the second angle 1012. The shape of the implant for anterior vaginal wall prolapse support 10 is basically symmetric with respect to the longitudinal axis 11.

The implant for anterior vaginal wall prolapse support 10 is made of macromolecular mesh which can be any macromolecular material with low inflammatory effect. In one embodiment of the present invention, the mesh is made of macroporous polypropylene with monofilament having pores of diameter larger than 75 μm which allows macrophage to pass through to eliminate microorganisms. In another embodiment of the present invention, the mesh can be made of heterogeneous material, such as collagen extract from swine intestinal mucosa.

In one embodiment of the present invention, the length from the first angle 1011 to the second angle 1012 of the implant for anterior vaginal wall prolapse support 10 is 7-10 cm, and preferably 8-9 cm; the length of the base of the first angle 1011 is 4-6 cm, and preferably 4.5-5.5 cm; the length of the base of the second angle 1012 is 6-8 cm, and preferable 6.5-7.5 cm.

In one preferred embodiment of the present invention, the first angle 1011 of the implant for anterior vaginal wall prolapse support 10 is an obtuse angle, and the degree of the first angle 1011 is greater than the degree of the second angle 1012; the two edges forming the first angle 1011 are equal, and the two edges forming the second angle 1012 are equal, resulting in the implant for anterior vaginal wall prolapse support 10 of the first body 101 being symmetrical with respect to the longitudinal axis 11.

In one embodiment of the present invention, each of the first arms 102 is disposed at each margin of the extended edge of the first angle 1011. In one preferred embodiment of the present invention, each of the second arms 103 is disposed at each edge forming the second angle 1012 resulting in the angle between the pair of second arms 103 and the longitudinal axis 11 not being a right angle.

Figure 2:
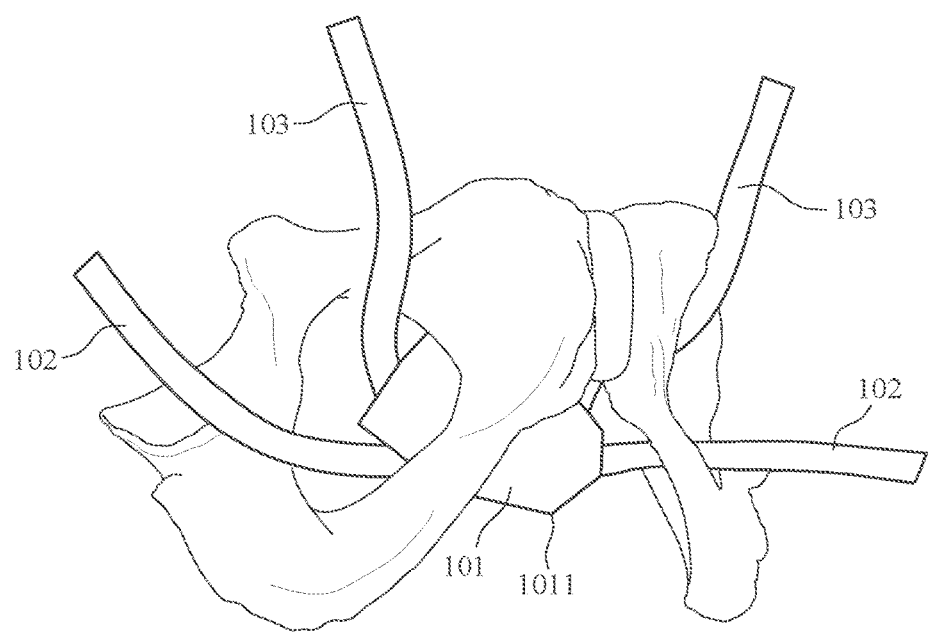
FIG. 2, schematic representation of the status when using the implant for anterior vaginal wall prolapse support 10 in FIG. 1.

Please refer to FIG. 2, the schematic representation of the status when using the implant for anterior vaginal wall prolapse support 10. As shown in FIG. 2, the first body 101 is placed underneath bladder with the first angle 1011 facing the front to support the prolapsed bladder and the pair first arms 102 and the pair of second arms 103 passing the obturator foramens for fixation. If the patient also suffers from SUI, the first angle 1011 can be placed underneath the bladder neck and proximal urethra to stop urine in the bladder from leaking by the upward pull of the first arms 102 during bladder contraction in voiding.

In light of the above features, the implant for cystocele support can effectively hold the prolapsed bladder and simultaneously treat female SUI.

Figure 3:
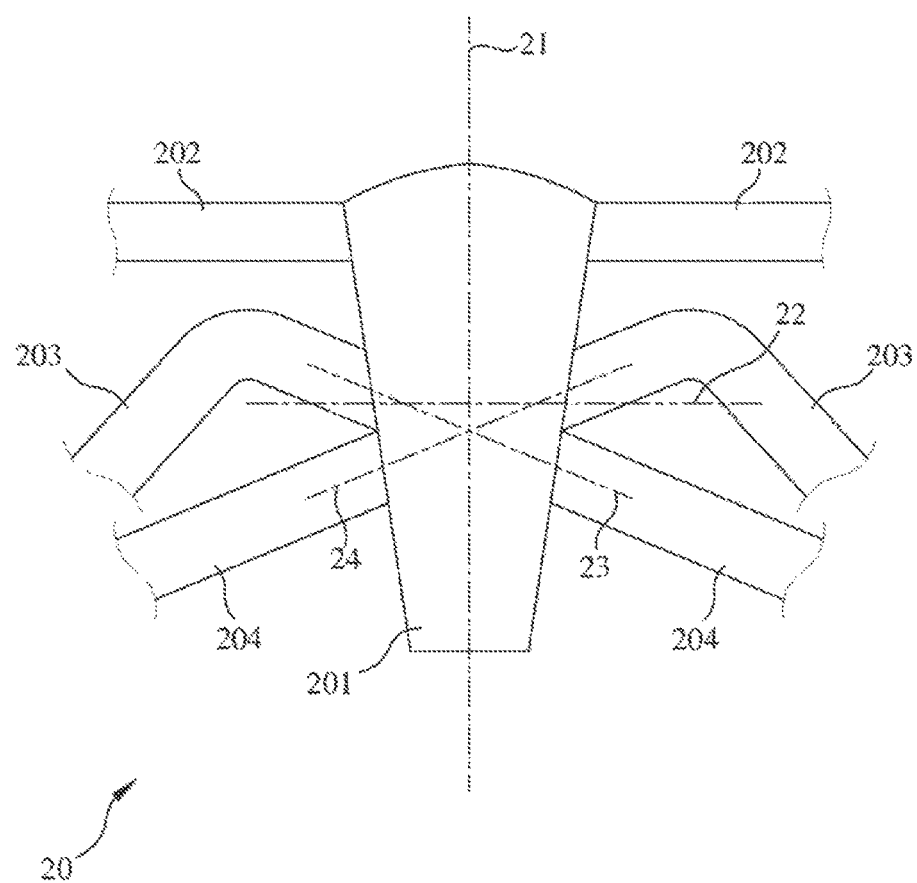
FIG. 3, schematic representation of the implant for posterior vaginal wall prolapse support of the present invention.

In one preferred embodiment of the present invention, the implant for POP support of the present invention can further comprise an implant for posterior vaginal wall prolapse support 20, as shown in FIG. 3. The implant for posterior vaginal wall prolapse support 20 comprises: a second body 201 having a shape of a longitudinal axis 21 greater than a horizontal axis 22; a pair of third arms 202 connecting with both sides of the longitudinal axis 21 of the second body 201, respectively; a pair of fourth arms 203 connecting with both sides of the longitudinal axis 21 of the second body 201, respectively, wherein the third arm 202 and the fourth arm 203 disposed at the same side of the longitudinal axis 21 are separated from each other; and a pair of fifth arms 204 connecting with both sides of the longitudinal axis 21 of the second body 201, the fourth arm 203 is located between the third arm 202 and the fifth arm 204 disposed at the same side of the longitudinal axis 21. The shape of the implant for posterior vaginal wall prolapse support 20 is basically symmetric with respect to the longitudinal axis 21. Furthermore, the fourth arm 203 disposed at one side of the longitudinal axis 21 is aligned with the fifth arm 204 disposed at another side of the longitudinal axis 21; thus, the prolongation 23/24 of the fourth arms 203 from a cross on the longitudinal axis 21.

In one preferred embodiment of the present invention, the fourth arm 203 and the fifth arm 204 are adjacent. The implant for posterior vaginal wall prolapse support 20 is made of macromolecular mesh which can be any macromolecular material with low inflammatory effect. In one embodiment of the present invention, the mesh is made of macroporous polypropylene with monofilament having pores of diameter larger than 75 μm which allows macrophage to pass through to eliminate microorganisms. In another embodiment of the present invention, the mesh can be made of heterogeneous material, such as collagen extract from swine intestinal mucosa.

In one embodiment of the present invention, the length between both ends of the longitudinal axis 21 on the implant for posterior vaginal wall prolapse support 20 is 9-11 cm, and preferably 10 cm; the widest width of the side close to the third arm 202 is 5-7 cm, and preferably 6 cm; the width of the side close to the fifth arm 204 is 3-5 cm, and preferably 4-5 cm.

In another embodiment of the present invention, the shape and width of the third arms 202, the fourth arms 203, or the fifth arms 204 are not limited and can be adjusted according to the sizes of patients' organs. The shape of the side close to the third arms 202 on the second body 201 is also not limited; they can be arc-shaped (as shown in FIG. 3) or flat.

Figure 4:
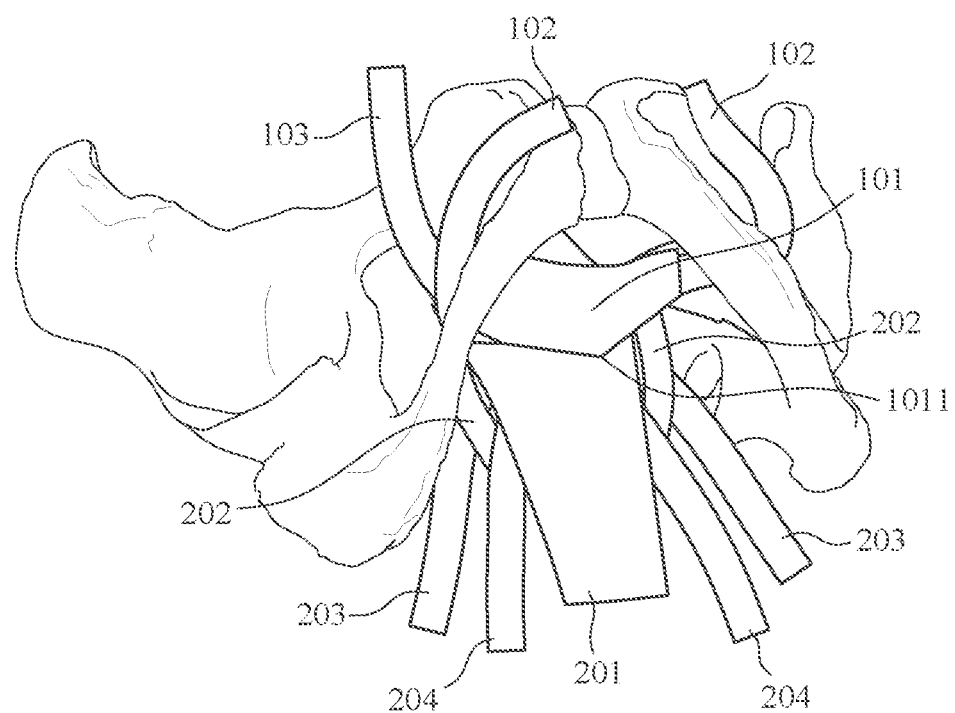
FIG. 4, schematic representation of the status when using the implant for anterior vaginal wall prolapse support 10 and the implant for posterior vaginal wall prolapse support 20 collaboratively (View from the lower right).
Figure 5:
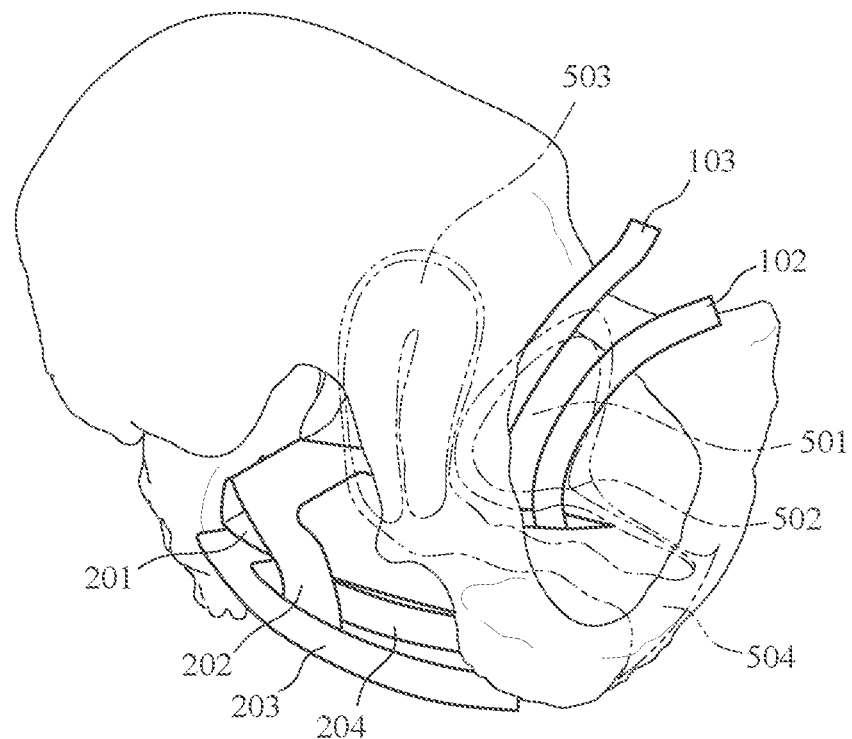
FIG. 5, schematic representation of the status when using the implant for anterior vaginal wall prolapse support 10 and the implant for posterior vaginal wall prolapse support 20 collaboratively (Side view).

Please refer to FIG. 4 and FIG. 5 for the schematic representation of the status when using the implant for anterior vaginal wall prolapse support 10 and the implant for posterior vaginal wall prolapse support 20 collaboratively, in which the setup for the implant for anterior vaginal wall prolapse support 10 to support bladder 501, bladder neck 502 and proximal urethra is illustrated in FIG. 2 and described hereinbefore. The front end of the second body 201 of the implant for posterior vaginal wall prolapse support 20 is banded upward and placed underneath the uterus to support the prolapsed uterus 503. The intersection of the prolongation 23/24 on the longitudinal axis 21 was placed at approximately 5-6 cm from vaginal introitus 504. The third arms 202 are inserted on both sides of the uterosacral ligament without tension forming a groove to support enterocele. The fourth arms 203 are inserted through bilateral sacrospinous ligaments, respectively. The fourth arms 203 and the fifth arms 204 were placed on both sides of the rectum and bended backwards for fixation, which simultaneously treats the rectocele.

Figure 6:
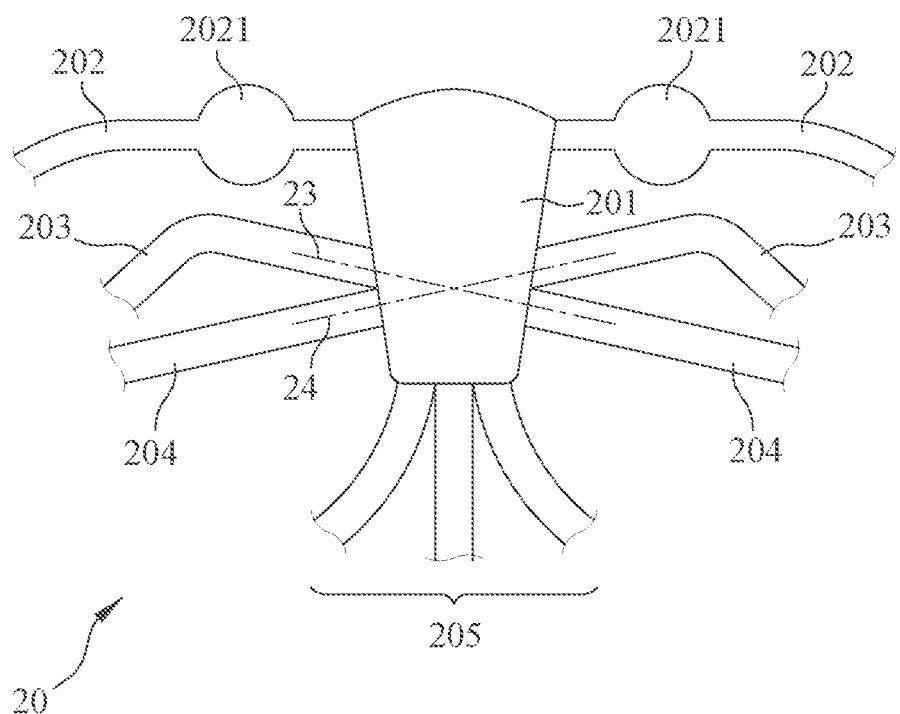
FIG. 6, schematic representation of the implant for posterior vaginal wall prolapse support of the present invention with the addition of the expansion portion and the set of sixth arms.

Please refer to FIG. 6 for the schematic representation of the implant for posterior vaginal wall prolapse support 20 of another embodiment of the present invention. As shown in FIG. 6, each of the third arms 202 has an expansion portion 2021 and the expansion portions 2021 of the third arms are disposed at symmetric locations, which can enhance the sideways supporting force when the above-mentioned groove is formed. Preferably, a shape of the expansion portion is circular.

Figure 7:
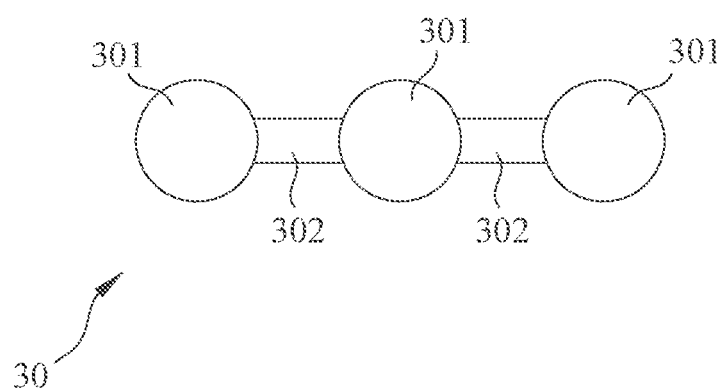
FIG. 7, schematic representation of the auxiliary supporter.

Besides, a set of sixth arms 205 can also be disposed at one end of the longitudinal axis of the second body 201 close to the pair of fifth arms 204. The number of arms of the set of sixth arms 205 is not limited and is preferably three. The set of sixth arms 205 are used jointly with an auxiliary supporter 30. However, the set of sixth arms 205 is not just a wide arm, an extension of the second body 201, and also not a complete sheet design, for the purposes of reducing resistance of intestinal tract and avoiding constipation. Please refer to FIG. 7 for the schematic representation of the auxiliary supporter 30. The auxiliary supporter 30 comprises a plurality of fixing components 301 and a plurality of linking components 302 interconnecting with the plurality of the fixing components 301. The plurality of fixing components 301 is used to fix the prolapsed anus, while the plurality of linking components 302 maintains the distance between each fixing components 301. Each of the sixth arms 205 is fixed to each fixing component 301 to keep each organ in the relatively normal position.

Because the set of sixth arms 205 is used jointly with the plurality of fixing components 301 of the auxiliary supporter 30, the number of the sixth arms is preferably equal to the number of the fixing components 301, but the circumstance of multiple arms being fixed to one fixing component is not excluded. Moreover, due to each of the sixth arms 205 being fixed to each fixing component 301, the width of each fixing component 301 is preferably greater or equal to the width of each of the sixth arms 205.

In one preferred embodiment of the present invention, the shape of the plurality of fixing components is circular. The auxiliary supporter is made of macromolecular mesh which can be any macromolecular material with low inflammatory effect. In one embodiment of the present invention, the mesh is made of macroporous polypropylene with monofilament having pores of diameter larger than 75 μm which allows macrophage to pass through to eliminate microorganisms. In another embodiment of the present invention, the mesh can be made of heterogeneous material, such as collagen extract from swine intestinal mucosa.

According to the above embodiments, the implant for anterior vaginal wall prolapse support 10 of the present invention can be used solely without uterine band due to the function of the first angle 1011 described above and can treat cystocele and SUI at one time. The implant for anterior vaginal wall prolapse support 10 and the implant for posterior vaginal wall prolapse support 20 can be used collaboratively for simultaneous treatment of cystocele, female SUI, enterocele, uterine prolapse, vaginal vault prolapse, and rectocele. Furthermore, with the addition of the sixth arms 205 and the auxiliary supporter 30, the implant of the present invention can also be used to treat anal prolapse simultaneously. Hence, the present invention provides ligamentous support of DeLancey's level I (Suspension), level II (Lateral attachment), and level III (Fusion), as well as reposition and fixation for the prolapsed bladder, urethra, uterus, small intestine, rectum, and anus, which, significantly reduce the surgical complexity, the number of implants used, and the occurrence of complications.

What is claimed is:

1. An implant for pelvic organ prolapse (POP) support, comprising an implant for anterior vaginal wall prolapse support which comprises:
   a first body having a first pair of straight edges and a second pair of straight edges, with a first angle between the first pair of straight edges and a second angle between the second pair of straight edges, the first and second angles being located at a first end and a second end respectively of a longitudinal axis of the first body, wherein the first angle of the implant for anterior vaginal wall prolapse support is an obtuse angle, the lengths of the first pair of straight edges are 4-6 cm, the lengths of the second pair of straight edges are 6-8 cm, and the distance between the first angle and the second angle is 7-10 cm;
   a pair of first arms connecting with both sides of the longitudinal axis of the first body, respectively, wherein each of the pair of first arms is disposed perpendicular to the longitudinal axis of the first body; and
   a pair of second arms connecting with both sides of the longitudinal axis of the first body, respectively, wherein the first arm and the second arm disposed at the same side of the longitudinal axis are separated from each other.

2. The implant of claim 1, wherein the implant for anterior vaginal wall prolapse support is a polymer mesh.

3. The implant of claim 1, wherein the degree of the first angle of the implant for anterior vaginal wall prolapse support is greater than the degree of the second angle of the implant for anterior vaginal wall prolapse support.

4. The implant of claim 1, wherein the lengths of the first pair of straight edges forming the first angle of the implant for anterior vaginal wall prolapse support are equal; the lengths of the second pair of straight edges forming the second angle of the implant for anterior vaginal wall prolapse support are equal.

5. The implant of claim 1, wherein each of the first arms of the implant for anterior vaginal wall prolapse support is disposed at each margin of two extended edges of the first pair of straight edges of the first angle of the implant for anterior vaginal wall prolapse support.

6. The implant of claim 1, wherein each of the second arms of the implant for anterior vaginal wall prolapse support is disposed at each edge of the second pair of straight edges of the second angle of the implant for anterior vaginal wall prolapse support.

* * * * *